United States Patent [19]

Wang et al.

[11] Patent Number: 4,833,071
[45] Date of Patent: May 23, 1989

[54] PEPTIDE COMPOSITION AS ANITGEN FOR DETECTION OF ANTIBODIES TO HTLV-I, AS A VACCINE FOR ATL AND METHODS THEREFOR

[75] Inventors: Chang Y. Wang, Great Neck; James J. G. Wang, Flushing; D. Wayne Walters, Mineola, all of N.Y.

[73] Assignee: United Biomedical, Inc., Lake Success, N.Y.

[21] Appl. No.: 1,885

[22] Filed: Jan. 9, 1987

[51] Int. Cl.$^4$ .......................... C07K 7/08; C07K 7/10; C12Q 1/70; B65D 69/00
[52] U.S. Cl. .......................................... 435/5; 435/7; 435/805; 435/810; 530/326; 530/327; 422/61
[58] Field of Search ....................... 435/5, 7, 860, 805; 530/325, 326; 422/61

[56] References Cited

U.S. PATENT DOCUMENTS

4,689,398  8/1987  Wu et al. ............................. 530/327

FOREIGN PATENT DOCUMENTS

WO8601834  3/1986  PCT Int'l Appl. ..................... 435/5

OTHER PUBLICATIONS

Sugamura et al, "Identification of a Glycoprotein, gp21, of Adult T Cell Leukemia Virus by Monoclonal Antibody", J. Immunol. 132(1984):3180-4.
Oroszlan et al, "Primary Structure and Processing of gag and env Gene Products of Human T-Cell Leukemia Viruses HTLV-I$_{CR}$ and HTLV-I$_{ATK}$", Current Topics in Microbiology and Immunology, 115(1985):221-233.
Kiyokawa et al, "Envelope proteins of Human T-cell leukemia virus: Expression in *Eschrichia coli* and its Application to Studies of env Gene Functions", Proc. Nat'l. Acad. Sci. USA, 81(1984):6202-6.
Hattori et al, "Identification of gag and env Gene Products of Human T-Cell Leukemia Virus (HTLV)", Virology, 136(1984):338-347.
Cianciolo et al, "Similarity between p15E of murine and feline leukemia viruses and p21 of HTLV", Nature, 311(1984):515.
Patarca et al, "Sequence Similarity among Retroviruses-Erratum", Nature, 309(1984):728.
B. J. Poiesz, et al., Proc. Natl Acad. Sci. USA, 77:7415, (1980).
B. J. Poiesz, F. W. Ruscetti, M. S. Reitz, V. S. Kalyanarman, R. Gallo, Nature (London), 294:268 (1981).

R. C. Gallo et al., Proc. Natl. Acad. Sci. USA, 79:5680 (1982).
M. Essex et al., Science, 221:1061 (1983).
P. Clapham, K. Napy, R. A. Weiss, Proc. Natl. Acad. Sci., 81:2886 (1984).
R. C. Gallo et al., Cancer Res., 43:3892 (1983).
W. A. Blattner, K. Tokatsuki, R. C. Gallo, J. Am. Med. Assoc., 250:1074 (1983).
K. Takatusuki, J. Uchiyama, K. Sagawa, J. Yodoi, Topics in Hematology, S. Seno, F. Takaku, S. Irino, Eds. (*Excerpta* Medica, Amsterdam, 1977) p. 73.
W. A. Blattner et al., Int. J. Cancer, 30:257 (1982).
D. Catovsky et al., Lancet, 1982-I, 639 (1982).
D. W. Blayney et al., J. Am. Med. Assoc., 250:1048 (1983).
M. Robert-Guroff, F. W. Ruscetti, L. W. Posner, B. J. Poiesz, R. C. Gallo, J. Exp. Med., 154:1957 (1981).
M. Robert-Guroff et al., J. Exp. Med., 157:248 (1983).
M. Shimoyama et al., Jpn. J. Clin. Oncol., 12:109 (1982).
M. Seiki, S. Hattori, Y. Hirayama, M. Yoshida Proc. Natl. Acad. Sci. USA, 80:3618 (1983).
Saxinger, C. W. et al., Science, 225:1473 (1984).
Samuel, K. P. et al., Science, Nov. 30, 1984, 1094–1097.
Wang, J. J-G, Steel, S., S., Wisniewolski, R. and Wang C. Y. Proc. Natl. Acad. Sci. USA, 83, pp. 6159–6163 (Aug. 1986).
D. J. Slamon et al. Science, 225 (Oct. 5, 1984).
J. Sodroski et al. Science, Jul. 27, 1984.
G. J. Cianciolo et al. Science, 230, pp. 453–455 (Oct., 1985).

*Primary Examiner*—Christine M. Nucker
*Attorney, Agent, or Firm*—Maria C. H. Lin

[57] ABSTRACT

The present invention relates to a method for the detection and diagonosis of ATL (adult T cell leukemia/-lypmphoma) condition by the use of chemically synthesized peptide composition. The peptide composition comprises peptides having amino acid sequences corresponding to segments of the envelope protein, p21, of HTLV-I and mixtures thereof. The peptide composition is highly immunoreactive with antibodies in sera of patients with ATL.

The detection method includes an enzyme-linked immunosorbent assey (ELISA), an immunoradiometric assay (IRMA), and other forms of immunoassay procedures such as enzyme immuno blotting assay on nitrocellulose paper and hemagglutination assay using the peptide composition as the antigen. The preferred detection method is ELISA.

16 Claims, No Drawings

PEPTIDE COMPOSITION AS ANITGEN FOR DETECTION OF ANTIBODIES TO HTLV-I, AS A VACCINE FOR ATL AND METHODS THEREFOR

INTRODUCTION

Human T-cell leukemia virus subgroup I is a retrovirus causatively linked to certain adult lymphoid malignancies, notably adult T-cell leukemia-lymphoma (ATL) (1-3). Antibodies that react with HTLV-I proteins have been found in sera of ATL patients. These antibodies recognize both the gag core antigens and the envelope proteins of the virus (4,5).

The present invention relates to a highly sensitive method for the detection of antibodies to HTLV-I in body fluids by the use of a synthetic peptide composition. The peptide composition is also useful as a vaccine for ATL by stimulating the production of antibodies of HTLV-I to provide protection against infection by HTLV-I in healthy mammals, including humans. The peptide composition comprises peptides having amino acid sequences which correspond to segments of the transmembrane portion of the envelope protein, designated gp21, and has been found to be highly immunoreactive with antibodies in sera of patients with ATL.

More specifically, the present invention is directed to the use of a peptide composition comprising chemically synthesized peptides selected from the group consisting of about twenty, twenty four, and sixteen amino acids in a prescribed sequence, analogues, segments and mixtures thereof, for the detection of antibodies to the HTLV-I in human body fluids of ATL or HTLV-I infected individuals. The detection methods include an enzyme-linked immunoadsorbent assay (ELISA), dot blotting on nitrocellulose paper and hemagglutionation using the peptides as the antigens. The preferred detection method is by ELISA.

BACKGROUND OF THE INVENTION

The human T cell leukemia-lymphoma viruses (HTLV) are a family of related retroviruses originally isolated from patients with T cell lymphoma and cutaneous manifestations. A particular subgroup of the family, type I, also known as HTLV-I, is linked as causative agents of malignancies which share clinical and epidemiologic features with the disease called adult T-cell leukemia-lymphoma(ATL) that occurs in certain regions of Japan (6-9), the Caribbean Basin (10,11) and in southwestern United States (12).

Although the mechanism of transmission of HTLV-I is currently unknown, horizontal transmission of HTLV is clearly implicated by molecular and epidemiologic analyses (13,14). HTLV-I seropositivity in regions endemic for ATL is elevated overall in the general population and further elevated among close family members of patients and in the recipients of blood transfusions (15,16).

This means that there is an urgent need for a safe, reliable and sensitive test to screen each blood sample before its inclusion in blood banks to isolate blood samples which have been contaminated with HTLV-I virus to avoid the inadvertent spread of the virus among patients who must receive blood transfusions, e.g. hemophiliacs and surgical patients.

The complete nucleotide sequence of the HTLV-I virus has been reported in 1983 (17). This report elucidated the structure of the HTLV-I virus at both the DNA level and the predicted protein level and permits further serological studies of different epitopes which may be present on the HTLV-I virus.

Simultaneously, Dr. Carl Saxinger at National Cancer Institute reported the use of the isolated HTLV-I virus as a solid-phase immunoadsorbent for the development of an enzyme immunoassay for the detection of HTLV-I antibodies in the African population (18).

It is further reported by Samuel et al. (19) that a combined cloning and expression system in E. Coli has been used to identify HTLV-I DNA encoded glycoproteins which react immunologically with antibodies in sera from ATL patients. HTLV-I DNA encoding the envelope protein was cleaved into fragments and inserted into an expression vector. The expression vectors were introduced into an E. coli host by transformation. One clone, designates as pKS400, a envelope protein product was found to be suitable for use as an immunoadsorbent to screen a group of 28 coded sera. Antibodies that recognized the bacterially synthesized HTLV-I envelope protein sequences were found in all sera that had been shown to have antibodies to HTLV-I by an ELISA assay with disrupted virions as the antigen (18).

Slamon et al, Application No. PCT/US 85/01803, published on Mar. 27, 1986 under Publication No. W086/01834, described polypeptides associated with immunogenic sites of HTLV-I as expression products of the X region of HTLV-I, a highly conserved region located between env and the 3' LTR of the virus. The proteins have a molecular weight of between 37 kd and 40 kd and were cloned and expressed as fusion proteins in E. coli. The resulting products wee purified and used in liquid phase immunoprecipitation tests to screen sera. The results indicate an accuracy of from about 77% to 87%. (20)

Synthetic peptides have been used increasingly to map antigenic or immunogenic sites on the surface of proteins and for use as possible vaccines. We have previously taken this approach to identify and characterize highly antigenic epitopes on the envelope proteins of HTLV-III and developed sensitive and specific immunoassays for the detection of antibodies to HTLV-III (21) A similar approach is employed in this invention to select and identify highly antigenic epitopes in HTLV-I. In selecting regions of the envelope protein for epitope analysis, two strategies were applied. First, regions that exhibited a relatively high conversation of amino acid sequence between HTLV-I and HTLV-II were sought. Second, multiple overlapping linear peptides covering whole regions of gp21, the transmembrane portion of the HTLV-I envelope protein, were synthesized and characterized. Three peptides, with the following sequences, and a mixture thereof were found to be highly immunoreactive with sera from patients with ATL:

| | |
|---|---|
| GLDLLFWEQGGLCKALQEQC-NH2 | (I) |
| QNRRGLDLLFWEQGGLCKALQEQC-NH2 | (II) |
| NRRGLDLLFWEQGGLC-NH2 | (III) | wherein:
A=Ala=alanine,
R=Arg=arginine,
D=Asp=aspartic acid,
G=Gly=glycine,
I=Ile=isoleucine, F=Phe=phenylalanine,
N=Asn=asparginine,
Q=Gln=glutamine,
E=Glu=glutamic acid,
L=Leu=leucine,
K=Lys=lysine,
S=Ser=serine,
W=Trp=tryptophan,
Y=Tyr=tyrosine,
V=Val=valine,
C=Cys=cysteine.

Assays for antibodies to HTLV-I based upon chemically synthesized peptides show several advantages over assays utilizing whole disrupted virus or bacterially produced immunoadsorbents. The peptides can easily be synthesized in gram quantities by using automated solid-phase methods, thus providing a reproducible antigen of high integrity with consistent yields. Isolation of antigens from biological systems precludes such reproducibility. More importantly, non-specific reactivities seen in non-HTLV-I infected individuals are likely due to the heterogeneity of the preparations used for assay. This is particularly true for assays using either the whole virus or Escherichia coli-derived recombinant products as immunoadsorbents. In these processes, the major histocompatibility antigens or endogenous bacterial proteins of the host cells are frequently copurified with the desired antigen virus or protein. Since antibodies to these contaminating antigens are frequently found in normal individuals, false-positive results cannot be eliminated by using current antigen isolation processes.

The assay of the present invention thus clearly eliminates the false-positive reactions encountered in the other methods and, at the same time, shows a high sensitivity to truly positive sera by the substantially increased signal-to-noise ratio. This increased signal-to-noise ratio likely results from the purity of the immunoadsorbent.

Furthermore, up to the present, no viable vaccine or method to provide protection against HTLV-I has been reported. The use of deactivated virus provokes fears of contracting the disease and would prevent its acceptability and use.

Similarly, the development of monoclonal and polyclonal antibodies to HTLV-I in mammals involves the use of HTLV-I as the immunogen and this presents unacceptable risks in the procedure.

It is, therefore, an objective of the present invention to develop a detection or diagnostic procedure that does not require the use of the virus or lysates thereof as a test reagent.

A further objective is to develop a test procedure that is highly sensitive and accurate.

Another objective is to develop a test that is highly sensitive so that very little test reagent or body fluid is needed to obtain an accurate result.

A further objective is to prepare a test reagent by chemical means. The synthetic reagent can then be used to detect the presence of antibodies to HTLV-I in body fluids and diagnose ATL, thereby avoiding the danger of exposure to the virus or segments thereof and the unnecessary proliferation of the virus.

Another objective is to develop a vaccine which when introduced into the body will stimulate production of antibodies to HTLV-I to provide protection against infection by HTLV-I in healthy mammals, including humans.

A further objective is to provide an immunogen which can be used for the development in mammals of monoclonal and polyclonal antibodies to HTLV-I which does not involve the use of HTLV-I as the immunogen.

REFERENCES

1. B. J. Poiesz., et al., *Proc. Natl Acad. Sci. USA.*, 77: 7415 (1980).
2. B. J. Poiesz., F. W. Ruscetti, M., S. Reitz., V. S. Kalyanaraman, R. Gallo, *Nature* (London) 294: 268 (1981).
3. R. C. Gallo et al., *Proc. Natl. Acad. Sci. USA.*, 79: 5680 (1982).
4. M. Essex et al., *Science*, 221: 1061 (1983).
5. P. Clapham, K. Napy, R. A. Weiss, *Proc. Natl. Acad. Sci.* 81: 2886 (1984).
6. R. C. Gallo et al., *Cancer Res.*, 43: 3892 (1983).
7. R. C. Gallo, *Cancer Surveys*, L. M. Franks et al. Eds, (University Press, Oxford, in press).
8. W. A. Blattner, K. Tokatsuki, R. C. Gallo. *J. Am. Med. Assoc.*, 250: 1074 (1983).
9. K. Takatsuki, J. Uchiyama, K. Sagawa, J. Yodoi, *Topics in Hematology*, S. Seno, F. Takaku, S. Irino, Eds. (*Excerpta Medica*, Amersterdam, 1977) p73.
10. W. A. Blattner et al., *Int. J. Cancer*, 30: 257 (1982)
11. D. Catovsky et al., *Lancet*, 1982-I, 639 (1982).
12. D. W. Blayney et al., *J. Am. Med. Assoc.*, 250: 1048 (1983).
13. M. Robert-Guroff, F. W. Ruscetti, L. W. Posner, B. J. Poiesz, R. C. Gallo, *J. Exp. Med.*, 154: 1957 (1981).
14. R. C. Gallo et al., *Proc. Natl. Acad. Sci. USA.*, 79: 5680 (1981).
15. M. Robert-Guroff et al., *J. Exp. Med.*, 157: 248 (1983).
16. M. Shimoyama et al, *Jpn. J. Clin. Oncol.*, 12: 109 (1982).
17. M. Seiki, S. Hattori, Y. Hirayama, M. Yoshida *Proc. Natl Acad. Sci. USA.*, 80: 3618 (1983).
18. Saxinger, C. W. et al., *Science*, 225: 1473 (1984).
19. Samuel, K. P. et al., *Science*, Nov. 30, 1984.
20. Slamon et al., PCT Patent Publication No. WO86/01834.
21. Wang, J.J-G, Steel, S., Wisniewolski, R. and Wang, C. Y. *Proc. Natl. Acad. Sci. USA*, 83, pp 6159–6163 (August 1986).

BRIEF DESCRIPTION OF THE INVENTION

According to the present invention, three peptides, each arranged in a specific sequence, have been made by solid phase peptide synthesis. These peptides have been found to be useful in a highly sensitive and accurate method for the detection of antibodies to HTLV-I in sera and body fluids and in the diagnosis of ATL. These peptides have also been found to be useful in stimulating producting of antibodies to HTLV-I in healthy mammals such as Balb/c mice.

According to the present invention, a peptide composition useful for the detection of antibodies to HTLV-I and diagnosis of ATL comprises a peptide selected from the group of peptides comprising:

| | |
|---|---|
| GLDLLFWEQGGLCKALQEQC-X | (I) |
| QNRRGLDLLFWEQGGLCKALQEQC-X | (II) |
| NRRGLDLLFWEQCCLC-X | (III) | wherein X is —OH or —NH₂, analogues, segments, mixtures and polymers thereof, wherein:
A=Ala;32 alanine,
R=Arg=arginine,
D=Asp=aspartic acid,
N=Asn=asparagine,
Q=Gln=glutamine,
E=Glu=glutamic acid,
L=Leu=leucine,
K=Lys=lysine,
G=Gly=glycine,
I=Ile=isoleucine,
F=Phe=phenylalanine,
S=Ser=serine,
W=Trp=trotophan,
Y=Tyr=tyrosine,
V=Val=valine,
C=Cys=cysteine.

The highly sensitive and accurate method of detecting antibodies to HTLV-I in body fluids and diagnosis of ATL comprises the following steps:

A. Preparing a peptide composition comprising a peptide selected from the group having the following amino acid sequences:

| | |
|---|---|
| GLDLLFWEQGGLCKALQEQC-X | (I) |
| QNRRGLDLLFWEQGGLCKALQEQC-X | (II) |
| NRRGLDLLFWEQGGLC-X | (III) | wherein X is —OH or —NH₂, analogues, segments and mixtures thereof; and

B. Using about 0.1 ug to about 20 ug per test in a buffer at a pH of about 7 to 10, of the peptide composition as the antigen in an immunoassay procedure.

Further, according to the present invention, the peptides when coupled to a protein or a polymer carrier or when polymerized to homo or hetero dimers or higher oligomers by cysteine oxidation, induced disulfide cross linking, or when polymerized to homo or hetero dimers or higher oligomers by use of homo or hetero function multivalent cross linking reagents, can be used to stimulate production of antibodies to HTLV-I in healthy mammals, including humans. The method comprises introducing an effective amount of the peptide composition including a mixture of these three peptides, conjugated to a carrier, such as human serum albumin or as a polymer, into the body of a healthy mammal by intraperitoneal or subcutaneous injection.

DETAILED DESCRIPTION OF THE INVENTION

In accordance with the present invention, three peptides have been chemically synthesized for the detection of antibodies of HTLV-I in body fluids and diagnosis of ATL, for the vaccination of healthy mammals by stimulating the production of antibodies to HTLV-I in healthy mammals, and for the development of both monoclonal and polyclonal antibodies to HTLV-I in mammals. These three peptides are arranged in the following sequences:

| | |
|---|---|
| GLDLLFWEQGGLCKALQEQC-X | (I) |
| QNRRGLDLLFWEQGGLCKALQEQC-X | (II) |
| NRRGLDLLFWEQGGLC-X | (III) | wherein X is —OH or —NH₂.

These peptides may comprise analogues or segments, i.e. a shorter or longer peptide chain by having more amino acids added to the terminal amino acids, e.g., —Gly—, —Gln—, —Asn— and —Cys— of the above sequence or hving a few less of the terminal amino acids from either terminal. It is expected that as long as the three dimensional conformation recognizable by the dominant antibodies to HTLV-I is preserved, analogues of the synthetic peptide may also comprise substitution and/or deletion of the recited amino acids of the above sequence.

The amino acid sequences of the polypeptides useful as test reagents for the detection of antibodies to HTLV-I in body fluids and diagnosis of ATL are selected to correspond to a partial segment of the amino acid sequence of the HTLV-I virus designated as p21, a part of gp61, defining the envelope protein of the HTLV-I virus.

The peptides useful as solid phase immunoadsorbent for the detection of antibodies HTLV-I were synthesized by the "classified" Merrifield method of solid phase peptide synthesis using Boc-amino acids to correspond to the following amino acid sequences:

| | |
|---|---|
| GLDLLFWEQGGLCKALQEQC-X | (I) |
| QNRRGLDLLFWEQGGLCKALQEQC-X | (II) |
| NRRGLDLLFWEQGGLC-X | (III) | wherein X is —OH or —NH₂.

Analogues of these three peptides can be prepared by varying the amino acid sequences either by adding, subtracting substituting, or deleting desired Boc-amino acid(s).

Following completion of assembly of the desired blocked peptide on the resin, the peptide-resin is treated with anhydrous hydrofluoric acid to cleave the benzyl ester linking the peptide to the resin in order to liberate the peptide. Functional groups of amino acids which are blocked during synthesis by benzyl-derived blocking groups are also cleaved from the peptide simultaneously. The free peptide is then analyzed and purified by high pressure liquid chromatography (HPLC) and characterized biochemically by amino acid analysis.

Similarly, synthesis of these peptides that have an amide group on its C-terminal end can be achieved by using 4-methylbenzhydrylamine resin according to the following scheme:

4-methylbenzhydrylamine resin

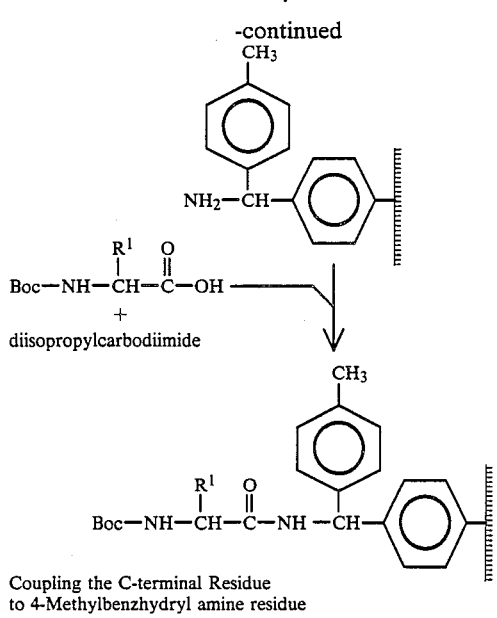

Coupling the C-terminal Residue
to 4-Methylbenzhydryl amine residue

The peptides synthesized according to the above described procedure are highly reactive to antibodies to HTLV-I and can be used as a highly sensitive and specific immunoadsorbent for the detection of the antibodies against HTLV-I. Results obtained with the peptides according to the present invention show that it is more sensitive and specific to antibodies against HTLV-I in body fluids than the lysates of density banded HTLV-I itself.

Tables I and II show the data obtained with sera from ATL patients using an ELISA method wherein the well plates are coated with a mixture of the peptides in a weight ratio of 1:1:1 (I:II:III) and deactivated HTLV-I. Table III compares the data obtained with sera from ATL patients using an ELISA method wherein the well plates are coated respectively with each of the three peptides as well as a mixture (1:1:1) thereof and disrupted HTLV-I.

Based on the high degree of sensitivity and specificity of the peptide composition according to the present invention in the immunoreaction to antibodies to HTLV-I, it is believed that the peptide composition may also be useful as a vaccine for ATL, and as immunogens for the development of both monoclonal and polyclonal antibodies to HTLV-I in mammals, including humans. The peptide composition when coupled to a protein or a polymer carrier or when polymerized to homo or hetero dimers or higher oligomers by cysteine oxidation, induced disulfide cross linking, or when polymerized to homo or hetero dimers or higher oligomers by use of homo or hetero functional multivalent cross linking reagents, can be introduced to normal subjects to stimulate production of antibodies to HTLV-I, and provide protection against infection by HTLV-I in healthy mammals. Since the peptide composition according to the present invention is not derived biochemically from the virus, there is no danger of exposing the normal subjects who are to be vaccinated to the disease.

The advantages of using the peptides according to the present invention are many.

The peptides are chemically synthesized. This means that there is no involvement with the HTLV-I virus at any time during the process of making the test reagent or the vaccine. During the preparation of the vaccine or the vaccination process, there is no risk of exposure of the production workers or individuals in the health profession to the HTLV-I virus. Similarly, there is no risk of exposure to HTLV-I in the use of these peptides or the development of monoclonal or polyclonal antibodies to HTLV-I in mammals. Further, up to the final step of the test to detect antibodies to HTLV-I, where the test reagent is exposed to samples of sera or body fluid, there is no risk of exposure of the laboratory worker to the HTLV-I virus. Any risk of exposure in this final step can be further avoided by taking the precautionary step of heating the serum samples, which are to be tested, at 60° C. for half an hour, thereby deactivating the virus.

Another problem which is avoided by the process of the present invention is the possibility of false positive results caused by the presence in antigenic materials from host cells co-purified with the HTLV-I viral preparation or E. Coli derived proteins co-purified with expressed viral fragments. Certain normal individuals have antibodies to E. Coli or human leukocyte antigens, e.g. HLA, which are cross reactive with the antigenic materials from host cells. Sera samples from these normal individuals even through they have not been exposed to HTLV-I, may show a positive response in the ELISA or IRMA tests.

A diagnosis that a person may be nfected with HTLV-I based on this type of false positive response can bring severe anxiety of the person and his/here family. All of these problems can be avoided by using the peptide composition of the present invention as the test reagents.

Further, with appropriate amino acid analogue substitutions, it is expected that various peptide analogues based on the prescribed amino acid sequence can be synthesized with properties giving rise to lower background readings or better adsorption capacity to solid phases useful for HTLV-I antibodies screening assays.

Moreover, because the peptide composition of the present invention is synthetically prepared, the quality can be controlled and as a result, reproducibility of the test results can be assured. Also, since very small amounts of peptides are required for each test procedure, and because the expense of preparing the peptide is relatively low, the cost of screening body fluids for antibodies to HTLV-I, and diagnosis of ATL and the preparation of a vaccine is relatively low.

The peptide prepared in accordance with the present invention can be used to detect HTLV-I infection and diagnose ATL by using it as the test reagent in an enzyme-linked immunoadsorbent assay (ELISA), an enzyme immunodot assay, a hemagglutination assay or a radioimmunoradiometric assay (IRMA). The preferred method is ELISA. The ELISA technique is exemplified in Example 1, the IRMA technique is exemplified in Examples 3, and the hemagglutination assay in Examples 4 and 5.

It is to be noted that in the following methods, 0.25% by weight of glutaraldehyde may be added in the coating buffer to facilitate better peptide binding onto the plates or beads. Further, horseradish peroxidase conjugated mouse monoclonal anti-human IgG antibody may be used in place of horseradish peroxidase conjugated goat anti human IgG (Fc) as second antibody tracer.

The gelatin used in these processes can include calf skin gelatin, pig skin gelatin, fish gelatin or any known available gelatin proteins or be replaced with albumin proteins.

EXAMPLE 1

Detection of Antibodies to HTLV-I by an Enzyme-Linked Immunoadsorbent Assay

Wells of 96-well plates were coated at 4° C. overnight (or 3 hours at room temperature), with a mixture of three peptides prepared as described in a ratio by weight of I:II:III=1:1:1, at 1.5 ug per well of the mixture in 100 ul 10 mM $NaHCO_3$ buffer, pH 9.5. The wells were washed three times with phosphate buffered saline (PBS) and then incubated with 250 ul of 3% by weight of gelatin in PBS at 37° C. for 1 hour to block non-specific protein binding sites, followed by three more washes with PBS containing 0.05% by volume of Tween 20. The test sera (blood taken from a human patient or normal individual) were diluted with PBS containing 20% by volume normal goat serum, 1% by weight gelatin and 0.05% by volume Tween 20 at dilutions of 1:20 and 1:200, volume to volume, respectively. 200 ul of the diluted sera were added to each well and allowed to react for 1 hour at 37° C. The wells were then washed three times with 0.05% by volume Tween 20 in PBS in order to remove unbound antibodies. Horseradish peroxidase conjugated goat anti-human IgG (Fc) was used as a second antibody tracer to bind with the HTLV-I antibody-antigen complex formed in positive wells. 100 ul of peroxidase labeled goat anti human IgG at a dilution of 1:3000 in 1% by volume normal goat serum, 0.05% by volume Tween 20 in PBS was added to each well and incubated at 37° C. for another 15 minutes.

The wells were washed five times with 0.05% by volume Tween 20 in PBS to remove unbound antibody and reacted with 100 ul of the substrate mixture containing 0.04% by weight orthophenylenediamine (OPD) and 0.012% by volume hydrogen peroxide in sodium citrate buffer, pH 5.0. This substrate mixture was used to detect the peroxidase label by forming a colored product. Reactions were stopped by the addition of 100 ul of 1.0M $H_2SO_4$ and the absorbance measured using an ELISA reader at 492 nm (i.e. $A_{492}$). Assays were performed in duplicate with one dilution (1:20) of serum samples from normal individuals or from patients with diseases unrelated to HTLV-1 infection used as negative controls. Absorbance readings greater than the cutoff value of $A_{492}=0.12$, (about 3×the mean $A_{492}$ value of normal serum control, were taken as positive. The results are shown in Table I.

TABLE I

Detection of Antibodies to HTLV-I by ELISA* Using a Mixture of Three Peptides as Solid Phase Immunoadsorbent

| | Subject | No. Positive/ No. Tested* | Percent Positive |
|---|---|---|---|
| 1. | Patients with ATL | 102/102 | 100.0% |
| 2. | Patients with AIDS/ARC or known to be infected with HTLV-III | 5/30 | 16.7% |
| 3. | Patients with autoimmune diseases | 0/12 | 0 |

TABLE I-continued

Detection of Antibodies to HTLV-I by ELISA* Using a Mixture of Three Peptides as Solid Phase Immunoadsorbent

| | Subject | No. Positive/ No. Tested* | Percent Positive |
|---|---|---|---|
| 4. | Normal subjects | 0/10 | 0 |

*Assay was performed using sera at 1:20 (v/v) dilution with buffer. The cutoff value was defined as $A_{492} = 0.12$, about three times (3X) the mean $A_{492}$ value of normal serum control.
Note:
Sera from patients with ATL were kindly provided by Dr. Kanji Miyamota of the Japanese Okayama Red Cross, sera from patients with AIDS, ARC Primary Immunodeficiency, Leukemia/Lymphomas were kindly provided by Dr. S. Gupta at the University of California at Irvine; Dr. D. M. Knowles at the New York University, and Dr. F. D. Siegal at the Long Island Jewish Hospital. Sera from patients with autoimmune diseases including Rheumatoid Arthritus, systemic Lupus Erythematosus and allergies were kindly provided by Dr. N. Chiorazzi at the Rockefeller University Hospital, New York.

The results in Table I show that the ELISA test procedure according to the present invention will sera samples is very accurate and highly specific. Although, about 16.7% of the AIDS/ARC or HTLV-III infected individuals were found also to be infected with HTLV-I, this is consistent with recent findings. These findings are alarming and effective measures are called for to prevent double infection by HTLV-I and HTLV-III. No immunoreactivity was found in normal subjects or patients who were identified as not being infected with HTLV-I.

It is to be noted that in screening tests to exclude virus contaminated blood from blood banks, the criteria for defining positive reactions may be made more stringent if desired.

EXAMPLE 2

The procedure of Example 1 was repeated using the same sera samples as in Example 1 except that the well plates were precoated with 1 ug per well heat inactivated NP40 solubilized HTLV-I. The results are presented in Table II.

TABLE II

Detection of Antibodies to HTLV-I by ELISA Using Heat Inactivated NP40 Solubilized HTLV-I as Solid Phase Immunoadsorbent

| | Subject | No. Positive/ No. Tested* | Percent Positive |
|---|---|---|---|
| 1. | Patients with ATL | 69/102 | 67.2 |
| 2. | Patients with AIDS and known to be infected with HTLV-III | 2/12 | 16.7 |
| 3. | Patients with autoimmune diseases | 0/12 | 0 |
| 4. | Normal subjects | 0/12 | 0 |

*The cutoff value is defined as the highest $A_{492}$ of normal serum control.

In comparison with results obtained in Example, 1, this method is much less accurate and specific and, therefore, less reliable. Furthermore, the cutoff value is selected using a much more liberal criteria.

EXAMPLE 3

Detection of Antibodies to HTLV-I by an Immunoradiometric Assay (IRMA)

Wells of 96-well flexible-polyvinylchloride (PV) plates are coated at 4° C. overnight (or 3 hours at room temperature) with a mixture (1:1:1) of these three peptides, prepared as described, at 1.5 ug per well in 100 ul 10 mM $NaHCO_3$ suffer, pH 9.5. The wells are washed three times with phosphate buffered saline (PBS) and then incubated with 250 ul of 3% by weight gelatin in PBS at 37° C. for 1 hour to block non-specific protein binding sites, followed by three more washed with PBS containing 0.05% by volume Tween 20. The test sera (blood taken from a human patient or normal individual) are diluted with PBS containing 20% by volume normal goat serum, 1% by weight gelatin and 0.05% by volumen Tween 20 at dilutions of 1:20 and 1:200 (volume to volume) respectively. 200 ul of the diluted sera are added to each cell and allowed to react for 1 hour at 37° C. The wells are then washed three times with 0.05% by volume Tween 20 in PBS in order to remove unbound antibodies. I-125 labeled affinity purified goat antihuman IgG (Fc) is used as a second antibody tracer that binds with the antibody-antigen complex formed in positive wells. 100 ul of I-125 labeled goat antihuman IgG of 50,000-200,000 cpm in 1% by volume normal goat serum, 0.05% by volume Tween 20 in PBS is added to each well and incubated at 37° C. for another hour.

The wells are washed five times with 0.05% by volume Tween 20 in PBS to remove unbound second antibody and dried. The wells are cut and counted by a gamma-scintillation counter. Assays are performed in duplicate with a 1:20 dilution volume to volume. Normal sera sample as negative controls are also tested simultaneously. Cpm readings greater than the average readings of normal sera samples+4SD (standard deviation ) are taken as positive.

EXAMPLE 4

Detection of Antibodies to HTLV-I by a Hemagglutination Assay using a mixture (1:1:1) of the three peptides coated gelatin articles, Erythrocytes of different animal species or latex beads as the solid phase immunoadsorbent One ml thoroughly washed erthrocytes, gelatin particles, a polystyrene latex beads are coated with the peptide mixture at concentrations in the range of 5 ug/ml to 1 mg/ml. The peptide mixture coated cells, particles or beads are then incubated with serially diluted serum samples in the wells of a 96-well U-shaped microplate. After being left at room temperature for about an hour, the agglutination patterns on the bottom are read, and the largest dilution showing a positive reaction is recorded.

This is a one-step assay which could be used for both qualitative and quantitative analysis of the presence of antibodies to HTLV-I in specimens including sera or biofluids.

EXAMPLE 5

A third test kit for detecting HTLV-I antibodies using the hemagglutination assay comprises a compartmented enclosure containing multiple 96-well U-shaped microplates and materials or hemagglutination assay including (1) a bottle of peptide mixture coated erythrocytes, gelatin particles or latex polystyrene beads; (2) normal human serum (as a negative control); and, (3) heat inactivated, NP40 solubilized seropositive ATL serum (as a positive control). The procedure described in Example 4 is to be followed.

EXAMPLE 6

A diagnostic test kit for HTLV-I antibodies detection can be constructed. The test kit comprises a compartmented enclosure containing multiple 96-well plates coated prior to use with 1.5 ug per well of the peptide mixture (1:1:1) of the present invention is 100 ul pH 9.5 10mM NaHCO$_3$ buffer. The kit further comprises materials for enzyme detection in separate sealed containers consisting of: (1) normal human serum (as negative control); (2) heat inactivated, NP40 solubilized HTLV-I seropositive ATL serum (as positive control); (3) normal goat serum; (4) peroxidase labeled-goat antihuman IgG; and (5) a color change indicator consisting of orthophenylenediamine (OPD) and hydrogen peroxide in phosphate citrate buffer. The procedure described in Example 1 is to be followed.

In this test, 96-well plates, precoated with the peptide of the present invention, can be replaced by polystyrene beads, or multiple mini-columns filled with controlled pore size glass beads, or nitrocellulose paper strip precoated with the peptides of the present invention for use as the solid phase immunoadsorbent.

EXAMPLE 7

A second test kit for detecting antibodies using the immunoradiometric assay (IRMA) comprises a compartmented enclosure containing multiple 96-well bendable polyvinylchloride (PVC) plates precoated with the peptide mixture (1:1:1) according to the present invention at a concentration of 1.5 ug per well of the peptide mixture in 100 ul of pH 9.5 10 mM NaHCO$_3$ buffer and materials for radioiommunoassay including: (1) normal human serum (as negative control); (2) heat inactivated, NP40 solubilized seropositive ATL serum (as positive control); (3) normal goat serum; and, (4) I-125 labeled goated anti human IgG. The procedure described in Example 3 is to be followed.

In this test kit, 96-well PVC plates precoated with the peptides of the present invention can be replaced by polystyrene beads precoated with the peptide of the present invention for use as the solid phase immunoadsorbent.

EXAMPLE 8

An experiment was conducted to compare ATL HTLV-I antibody results using individual peptides and a mixture (1:1:1) thereof in the procedure of Example 1 and heat inactivated, NP40 solubilized HTLV-I according to Saxinger et al. Sera from patients with ATL or HTLV-I infected asymptomatic individuals were diluted 1:20. Duplicates of each diluted sera sample were tested against the peptides according to the present invention and cultured HTLV-1 according to Saxinger et al. Normal human serum and heat inactivated HTLV-I seropositive ATL serum were used as controls. The results are shown in Table III.

TABLE III

COMPARISON OF A$_{492}$/CUT OFF RATIO FOR 102 HTLV-I POSITIVE SERA USING PEPTIDES I, II, III, MIXTURE THEREOF AND DISRUPTED HTLV-I AS SOLID PHASE IMMUNOADSORBENT

| LOT NO. | SAMPLE NO. | DISRUPTED HTLV-I | PEPTIDE | | | 1:1:1 |
|---|---|---|---|---|---|---|
| | | | I | II | III | I + II + III |
| I | 1 | 1.49 | 0.14 | 7.53 | 0.72 | 3.77 |
| | 2 | 1.88 | 12.17 | 30.72 | 4.78 | 36.23 |
| | 3 | 1.61 | 0.72 | 2.90 | 1.30 | 4.35 |
| | 4 | 1.54 | 4.78 | 28.40 | 5.94 | 37.54 |
| | 5 | 1.91 | 6.38 | 33.04 | 30.14 | 37.97 |
| | 6 | 1.70 | 13.19 | 1.30 | 1.45 | 1.59 |
| | 7 | 1.85 | 0.14 | 30.14 | 28.11 | 37.10 |
| | 8 | 1.84 | 11.30 | 6.52 | 2.02 | 10.14 |
| | 9 | 1.16 | 1.16 | 3.77 | 1.01 | 4.35 |

TABLE III-continued

COMPARISON OF $A_{492}$/CUT OFF RATIO FOR 102 HTLV-I POSITIVE SERA USING PEPTIDES I, II, III, MIXTURE THEREOF AND DISRUPTED HTLV-I AS SOLID PHASE IMMUNOADSORBENT

| LOT NO. | SAMPLE NO. | DISRUPTED HTLV-I | PEPTIDE I | PEPTIDE II | PEPTIDE III | 1:1:1 I + II + III |
|---|---|---|---|---|---|---|
|  | 10 | 1.68 | 1.16 | 6.96 | 1.16 | 8.99 |
|  | 11 | 1.67 | 20.43 | 2.17 | 1.59 | 2.75 |
|  | 12 | 2.37 | 18.70 | 12.60 | 3.62 | 18.40 |
|  | 13 | 1.79 | 16.20 | 30.00 | 3.48 | 37.10 |
|  | 14 | 2.11 | 13.30 | 3.33 | 12.75 | 17.68 |
|  | 15 | 1.55 | 3.91 | 6.23 | 1.16 | 3.91 |
|  | 16 | 1.21 | 2.32 | 2.03 | 0.72 | 1.74 |
|  | 17 | 1.49 | 1.74 | 3.48 | 1.16 | 4.06 |
|  | 18 | 1.49 | 7.39 | 2.90 | 1.74 | 2.32 |
|  | 19 | 1.48 | 26.30 | 2.90 | 2.61 | 20.72 |
|  | 20 | 1.27 | 1.88 | 6.52 | 1.88 | 7.25 |
| II | 1 | 0.00 | 0.14 | 2.03 | 1.30 | 3.19 |
|  | 2 | 0.91 | 14.05 | 8.99 | 12.17 | 24.06 |
|  | 3 | 1.88 | 0.00 | 3.62 | 1.59 | 1.59 |
|  | 4 | 0.67 | 20.14 | 5.94 | 10.00 | 12.46 |
|  | 5 | 2.00 | 928.99 | 10.50 | 2.61 | 6.23 |
|  | 6 | 1.69 | 0.00 | 8.84 | 1.59 | 9.13 |
|  | 7 | 1.10 | 17.40 | 16.23 | 23.77 | 42.03 |
|  | 8 | 1.03 | 2.61 | 14.78 | 17.10 | 11.88 |
|  | 9 | 1.21 | 0.72 | 1.59 | 1.59 | 1.59 |
|  | 10 | 0.85 | 2.61 | 2.03 | 2.17 | 3.48 |
|  | 11 | 0.94 | 5.36 | 17.83 | 28.40 | 24.93 |
|  | 12 | 1.25 | 3.48 | 21.30 | 13.04 | 30.87 |
|  | 13 | 1.52 | 24.63 | 26.09 | 3.04 | 30.87 |
|  | 14 | 1.91 | 7.10 | 13.38 | 31.74 | 36.81 |
|  | 15 | 0.42 | 1.30 | 6.38 | 3.19 | 8.70 |
|  | 16 | 1.25 | 0.00 | 4.64 | 3.19 | 6.96 |
|  | 17 | 1.40 | 0.87 | 20.72 | 11.16 | 20.58 |
|  | 18 | 0.015 | 0.00 | 1.30 | 1.74 | 1.59 |
|  | 19 | 1.81 | 4.35 | 34.06 | 34.49 | 35.80 |
|  | 20 | 1.37 | 0.00 | 4.78 | 1.16 | 7.10 |
|  | 21 | 1.79 | 0.14 | 7.54 | 1.45 | 3.91 |
|  | 22 | 1.26 | 0.14 | 2.90 | 1.88 | 3.33 |
|  | 23 | 0.90 | 2.75 | 7.10 | 6.67 | 9.71 |
|  | 24 | 0.73 | 0.29 | 1.74 | 2.32 | 2.32 |
|  | 25 | 0.96 | 0.00 | 3.33 | 1.30 | 3.91 |
|  | 26 | 1.34 | 0.00 | 6.52 | 2.03 | 4.20 |
|  | 27 | 1.55 | 11.74 | 22.17 | 31.16 | 36.67 |
|  | 28 | 2.03 | 21.74 | 33.33 | 32.46 | 38.41 |
|  | 29 | 1.49 | 27.97 | 25.94 | 8.26 | 35.80 |
|  | 30 | 1.69 | 3.48 | 3.04 | 1.45 | 3.19 |
|  | 31 | 1.55 | 5.94 | 8.99 | 3.33 | 30.14 |
|  | 32 | 1.58 | 13.04 | 17.10 | 1.88 | 13.19 |
|  | 33 | 1.43 | 6.23 | 16.67 | 1.88 | 17.97 |
|  | 34 | 1.33 | 0.00 | 2.46 | 2.57 | 3.04 |
|  | 35 | 1.60 | 3.91 | 7.39 | 14.35 | 13.04 |
|  | 36 | 1.42 | 0.00 | 10.58 | 2.61 | 25.80 |
|  | 37 | 1.22 | 0.43 | 1.88 | 1.74 | 2.03 |
|  | 38 | 0.70 | 0.00 | 1.88 | 1.74 | 4.35 |
|  | 39 | 1.49 | 10.29 | 16.23 | 1.74 | 26.23 |
|  | 40 | 1.94 | 10.58 | 14.64 | 14.78 | 24.05 |
|  | 41 | 1.73 | 15.36 | 20.29 | 14.35 | 35.65 |
|  | 42 | 1.54 | 0.00 | 1.16 | 1.16 | 1.45 |
|  | 43 | 1.70 | 0.00 | 1.59 | 1.74 | 1.88 |
|  | 44 | 0.49 | 0.00 | 2.32 | 2.32 | 2.90 |
|  | 45 | 0.52 | 0.00 | 1.74 | 1.88 | 2.03 |
|  | 46 | 0.96 | 0.72 | 2.32 | 1.59 | 7.10 |
|  | 47 | 1.79 | 28.99 | 35.94 | 24.50 | 37.68 |
|  | 48 | 1.18 | 0.58 | 3.33 | 2.03 | 2.61 |
|  | 49 | 1.72 | 8.40 | 17.25 | 2.18 | 15.79 |
|  | 50 | 1.10 | 0.00 | 1.45 | 1.74 | 2.32 |
|  | 51 | 1.63 | 8.41 | 15.94 | 1.45 | 19.57 |
|  | 52 | 1.40 | 0.43 | 1.74 | 1.88 | 2.75 |
|  | 53 | 1.10 | 0.00 | 3.04 | 2.46 | 3.33 |
|  | 54 | 1.31 | 1.74 | 5.80 | 1.16 | 8.26 |
|  | 55 | 0.46 | 0.72 | 2.60 | 2.02 | 3.3 |
|  | 56 | 0.60 | 3.19 | 4.64 | 2.17 | 5.80 |
|  | 57 | 0.40 | 0.87 | 3.48 | 2.02 | 33.33 |
|  | 58 | 0.72 | 9.86 | 14.20 | 1.74 | 25.07 |
|  | 59 | 0.46 | 0.00 | 2.90 | 0.72 | 4.20 |
|  | 60 | 0.49 | 0.00 | 1.74 | 1.74 | 4.20 |
|  | 61 | 0.48 | 7.83 | 12.6 | 3.04 | 12.17 |
|  | 62 | 0.39 | 0.29 | 1.88 | 1.45 | 3.77 |
|  | 63 | 0.34 | 2.17 | 6.09 | 3.49 | 8.55 |
|  | 64 | 0.40 | 0.14 | 1.88 | 1.59 | 3.48 |
|  | 65 | 0.37 | 17.2 | 18.69 | 11.30 | 35.65 |
|  | 66 | 0.10 | 0.87 | 1.45 | 1.16 | 1.45 |
|  | 67 | 1.68 | 0.58 | 8.99 | 1.88 | 14.20 |
|  | 68 | 1.46 | 0.00 | 1.88 | 1.74 | 2.32 |
|  | 69 | 0.61 | 1.59 | 9.13 | 2.46 | 13.76 |
|  | 70 | 0.76 | 11.01 | 14.92 | 9.69 | 32.61 |
|  | 71 | 1.54 | 0.43 | 1.56 | 2.03 | 3.04 |
|  | 72 | 0.63 | 0.43 | 2.17 | 1.88 | 2.60 |
|  | 73 | 2.03 | 23.77 | 36.96 | 20.29 | 28.89 |
|  | 74 | 0.72 | 0.00 | 1.16 | 10.14 | 1.45 |
|  | 75 | 0.54 | 0.00 | 1.45 | 1.30 | 2.46 |
|  | 76 | 1.19 | 0.29 | 2.17 | 1.74 | 2.03 |
|  | 77 | 2.34 | 0.00 | 8.41 | 1.88 | 4.06 |
|  | 78 | 1.64 | 3.62 | 6.67 | 6.96 | 11.30 |
|  | 79 | 1.70 | 6.96 | 9.57 | 1.59 | 5.94 |
|  | 80 | 1.74 | 7.10 | 14.2 | 2.03 | 11.01 |
|  | 81 | 1.57 | 10.5 | 26.1 | 12.0 | 30.14 |
|  | 82 | 0.86 | 1.59 | 3.33 | 1.74 | 4.92 |

The results in Table III show that the method is highly sensitive and specific. The ratio of $A_{492}$: Cutoff values achieved using the peptide composition of the present invention against ATL sera samples at the same dilution is often much higher than that achieved using deactivated HTLV-I against identical sera samples at identical dilutions. This is particularly true when a mixture (1:1:1) by weight of the peptides was used as the immuno-adsorbent. The data also show the peptide composition in the form of a mixture is highly accurate and no false negative results were obtained.

It is to be understood tht the above examples are illustrative of the present invention and are not meant to limit the scope thereof.

We claim:

1. A peptide composition having specific immunoreactivity to antibodies to HTLV-I comprising a peptide selected from the group consisting of:

GLDLLFWEQGGLCKALQEQC-X       (I)

QNRRGLDLLFWEQGGLCKALQEQC-X   (II)

NRRGLDLLFWEQGGLC-X           (III)

wherein X is —OH or —NH$_2$, analogues therefore wherein the amino acids in the sequence are substituted as long as the immunoreactivity to antibodies to HTLV-I derived from the three dimensional conformation of the sequences are substantially preserved; and mixtures and polymers of the peptides.

2. A peptide composition according to claim 1, comprising a mixture of the peptides I, II and III wherein I: II: III is in a ratio of 1:1:1 and each peptide is present in an amount of 0.1–20 μg.

3. An immunoassay method for the detection of antibodies to HTLV-OI and diagnosis of ATL conditions comprising:

A. coating a solid support with an effective amount of a peptide composition comprising a peptide selected from the group consisting of:

GLDLLFWEQGGLCKALQEQC-X (I)

QNRRGLDLLFWEQGGLCKALQEQC-X (II)

NRRGLDLLFWEQGGLC-X (III)

where X is —OH or —NH$_2$, analogues therefore wherein the amino acids in the sequence are substituted as long as the immunoreactivity to antibodies to HTLV-I derived from the three dimensional conformation of the sequencs are substantially preserved; and mixtures and polymers thereof as the antigen;

B. adding a test sera diluted with a buffer wherein the antibodies to HTLV-I in the test sera form a peptide-antibody complex with the peptide composition;

C. incubating the mixture at room temperature; and

D. detecting the presence of the peptide-antibody complex.

4. An immunoassay method according to claim 3 wherein the solid support is coated with a mixture of the peptides I, II and II wherein I: II: III is in a ratio of 1:1:1 and each peptide is present in an a mount of 0.1–20 μg.

5. An immunoassay method according to claim 4 wherein step D comprises: introducing a second known antibody labelled with an enzyme and a substrate which reacts with the enzyme to form a colored product.

6. An immunoassay method according to claim 4 wherein step D comprises: introducing a second known antibody labelled with a radiactive element.

7. An immunoassay method according to claim 4 wherein the peptide-antibody complex is detectable as an agglutination.

8. An immunoassay method according to claim 4 wherein the solid support is a strip coated with the peptide composition in a multidot array.

9. An immunoassay method according to claim 3 wherein step D comprises: introducing a second known antibody labelled with an enzyme and a substrate which reacts with the enzyme to form a colored product.

10. A method according to claim 9 wherein for each test, the peptide composition is a mixture of I: II: III and wherein each peptide is present in a range of 0.1 to 20 ug.

11. A method according to claim 10 wherein for each test, the ratio by weight of the three peptides I: II: III is 0.5 ug:0.5 ug:0.5 ug.

12. A method according to claim 11 wherein for each test, about 1.5 ug of the peptide mixture in a buffer at pH of about 7 to 10 is used as the antigen.

13. An immunoassay method according to claim 3 wherein step D comprises: introducing a second known antibody labelled with a radioactive element.

14. An immunoassay method according to claim 3 wherein the peptide-antibody complex is detectable as an agglutination.

15. An immunoassay method according to claim 3 wherein the solid support is a strip coated with the peptide composition in a multidot array.

16. A test kit for the detection of antibodies to HTLV-I and the diagnosis of ATL comprising:

a. a solid support;
b. coated onto the solid support, an immunoadsorbent comprising a peptide composition according to claim 1;
c. a sample of normal serum as negative control;
d. a sample of serum containing antibodies to HTLV-I as positive control; and
e. a buffer for diluting the serum samples.

* * * * *